(12) United States Patent
Mowry et al.

(10) Patent No.: US 7,078,237 B1
(45) Date of Patent: Jul. 18, 2006

(54) MICROPYROLYZER FOR CHEMICAL ANALYSIS OF LIQUID AND SOLID SAMPLES

(75) Inventors: Curtis D. Mowry, Albuquerque, NM (US); Catherine H. Morgan, Ann Arbor, MI (US); Ronald P. Manginell, Albuquerque, NM (US); Gregory C. Frye-Mason, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 376 days.

(21) Appl. No.: 10/035,537

(22) Filed: Oct. 23, 2001

(51) Int. Cl.
*G01N 25/20* (2006.01)
(52) U.S. Cl. .................. 436/147; 436/155; 250/288
(58) Field of Classification Search ............. 436/147, 436/155; 250/288
See application file for complete search history.

(56) References Cited

U.S. PATENT DOCUMENTS

| | | | |
|---|---|---|---|
| 3,954,819 A * | 5/1976 | Husch | 554/193 |
| 3,992,174 A | 11/1976 | Nakamura et al. | |
| 4,408,125 A * | 10/1983 | Meuzelaar | 250/288 |
| 4,710,354 A * | 12/1987 | Behar et al. | 422/80 |
| 4,837,374 A | 6/1989 | Brown et al. | |
| 4,980,131 A | 12/1990 | Meuzelaar et al. | |
| 5,367,164 A * | 11/1994 | Schultz | 250/288 |
| 5,472,670 A | 12/1995 | Harrington et al. | |
| 5,550,062 A * | 8/1996 | Wohltjen et al. | 436/155 |
| 6,171,378 B1 | 1/2001 | Manginell et al. | |
| 6,627,881 B1 * | 9/2003 | Bertrand et al. | 250/288 |

OTHER PUBLICATIONS

Martin, et al., "Gas Sensing with Acoustic Devices," 1996 IEEE Ultrasonics Symposium, Nov. 1996, 423-433.

Morgan, et al., "Rapid identification of bacteria with miniaturized pryolysis/GC analysis," Proceedings of SPIE, vol. 4205, Nov. 2000, 199-206, Oct. 15,1995, 11 744-11 751.

Matzke, et al., "Microfabricated silicon gas chromatographic micro-channels: fabrication and performance," Proceedings of SPIE, vol. 3511, Sep. 1998, 262-267.

Manginell, et al., "Microfabrication of membrane-based devices by HARSE and combined HARSE/wet etching", 8 pages.

Manginell, et al. "Finite Element Modeling of a Microhotplate for Microfluidic Applications," 4 pages.

Frye-Mason, et al. "Integrated Chemical Analysis Systems for Gas Phase CW Agent Detection," 5 pages.

Cavicchi, et al. "Micro-hotplate Gas Sensor," Solid State Sensor and Actuator Workshop, Hilton Head, SC, Jun. 12-16, 1994, 53-56.

Manginell, et al. "An overview of micromachined platforms for thermal sensing and gas detection," SPIE vol. 3046, 1997, 273-284.

* cited by examiner

*Primary Examiner*—Jill Warden
*Assistant Examiner*—LaToya C. Younger
(74) *Attorney, Agent, or Firm*—Kevin W. Bieg (57) ABSTRACT

A micropyrolyzer has applications to pyrolysis, heated chemistry, and thermal desorption from liquid or solid samples. The micropyrolyzer can be fabricated from semiconductor materials and metals using standard integrated circuit technologies. The micropyrolyzer enables very small volume samples of less than 3 microliters and high sample heating rates of greater than 20° C. per millisecond. A portable analyzer for the field analysis of liquid and solid samples can be realized when the micropyrolyzer is combined with a chemical preconcentrator, chemical separator, and chemical detector. Such a portable analyzer can be used in a variety of government and industrial applications, such as non-proliferation monitoring, chemical and biological warfare detection, industrial process control, water and air quality monitoring, and industrial hygiene.

13 Claims, 8 Drawing Sheets

Derivatization

FATTY ACID  DERIVATIZING REAGENT  SALT

Pyrolysis

FATTY ACID METHYL ESTER

MICROPYROLYZER FOR CHEMICAL ANALYSIS OF LIQUID AND SOLID SAMPLES

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates to a pyrolyzer and use thereof, and more particularly, to a micropyrolyzer capable of pyrolysis, heated chemistry, or thermal desorption of small liquid and solid samples for subsequent gas phase chemical analysis.

Pyrolysis is the rapid decomposition or dissociation by thermal energy of materials into smaller chemical fragments. As a sample preparation and introduction technique, pyrolysis can be performed on a wide variety of samples ranging from aerosols and complex polymers to biological samples. By such rapid heating, solids can be decomposed or dissociated, liquids can be vaporized, and species within a liquid can also be decomposed. In practice, programmed temperatures from 300 to 1000° C. are applied to the liquid or solid sample in a short time duration, typically ranging from milliseconds to a few seconds. The gas phase products of the sample pyrolysis are usually introduced or transferred into another device for some type of chemical analysis. These analysis devices can include a gas chromatograph (GC), mass spectrometer (MS), spectrophotometer, or other chemical analysis separator and/or detector. While these analysis devices are being reduced in size for commercial use, currently available commercial pyrolyzers require large power sources that are not compatible with field use. In addition, conventional pyrolyzers use metal wires or foils for heating, which may be incompatible with some sample materials.

There are several types of instrumentation used to perform pyrolysis, including gas chromatographic inlet, infrared, Curie-point, and resistive pyrolyzers. In gas chromatographic inlet pyrolysis, a liquid sample is introduced into the heated inlet of a commercial gas chromatograph and vaporized for subsequent analysis. In the infrared pyrolysis method, pulsed infrared laser radiation rapidly heats the sample, depending upon the irradiance or energy per unit area focused upon the sample during the pulse. In Curie-point pyrolysis, a magnetic metal foil or wire of particular alloy composition is excited by radio frequency energy. The metal heats until the characteristic Curie-point temperature of the alloy is reached, at which point the metal is no longer magnetic and ceases to heat. Resistive pyrolysis is perhaps the simplest of the common pyrolysis methods, requiring only a metal filament (often platinum) and a capacitive power supply capable of sending a large current rapidly through the filament.

Heated chemistry is used to derivatize (chemically react) an analyte to form a new species that has enhanced properties for analysis in a gas chromatograph or other analysis unit. The new species is often more volatile, or may have more desirable properties for subsequent detection (such as adding chlorine for electron capture detection). The derivative chemistry reactions are often performed in separate glassware, followed by injection into the gas chromatograph for vaporization and analysis.

Thermal desorption is a common technique for recovering (for analysis) volatile and semi-volatile chemical species from solid samples. Examples include gasoline components from soils, phthalates from plastic components, and volatile organic compounds (VOCs) from many types of solids. Heating is usually limited to an upper limit of about 350° C. due to the polymeric gaskets used to connect the heating device to the analytical instrument.

Pyrolysis, heated chemistry, and thermal desorption for chemical analysis have applications both in the standard laboratory and in field use. Applications of interest to the government include non-proliferation monitoring, counter-terrorism and first responder efforts, and chemical and biological warfare agent detection. Applications of interest to industry include efficient industrial process control, emissions control, water and air quality monitoring, food and water safety, agricultural quality control, biomedical diagnostics, and law enforcement activities such as drug and forensic analyses. Additional applications include the analysis and/or identification of bacteria, fungi, micro-organisms, and various pathogens and pathogenic activity in both animals and plants for food and water safety, biologically active process monitoring, and industrial hygiene.

Conventional pyrolyzers have several shortcomings for many of these applications. Conventional pyrolyzers can require large power supplies and control units and costly equipment. For example, a commercially available Curie-point pyrolyzer can require tens of Watts of power, occupy over 10,000 $cm^3$ of space, and weigh nearly 20 kg. In particular, due to increased regulations, cost issues, and public concern, there exists a need for field portable analyzers for on-site contamination detection and remediation, process control, emission monitoring, and other applications.

The micropyrolyzer of the present invention enables the development of a truly portable, self-contained (e.g., battery operated) pyrolysis-based analyzer that is not available with conventional analysis devices. The ability of the micropyrolyzer to be integrated with other on-chip components allows reduced operation, manufacture, and replacement costs; increased flexibility; and increased portability. Furthermore, the micropyrolyzer can be constructed from semiconductor materials, thereby enabling analysis of chemical samples that may be reactive with the metal wire or foil heating elements of conventional pyrolyzers. For pyrolysis, the micropyrolyzer allows smaller samples with lower dead volumes to be heated to higher temperatures, reducing sample consumption and power requirements and providing a wider range of available procedures. For heated chemistry, the micropyrolyzer enables derivatization and vaporization of a small sample to be performed in the same device. For thermal desorption from solids, the micropyrolyzer enables a needed portable field unit.

SUMMARY OF THE INVENTION

The present invention is directed to a micropyrolyzer for vaporization or pyrolyzation of a liquid or solid sample, comprising a substrate having a suspended membrane formed thereon, the membrane having a top side facing the substrate for accepting the liquid or solid sample; and a resistive heating element disposed on the membrane such that the sample will be vaporized upon heating of the membrane by the resistive heating element. The micropyrolyzer can be fabricated of semiconductor materials and metals.

The invention is further directed to a method for pyrolyzing a liquid or solid sample for analysis, comprising depositing the sample on the pyrolysis stage of a micropyrolyzer; heating the sample in the micropyrolyzer so as to vaporize the sample; and removing the vaporized product of the sample through an outlet of the micropyrolyzer to a chemical analysis unit. The sample size can be less than 3 microliters and the sample heating rate can be greater than 20° C. per millisecond.

The invention is further directed to a portable analyzer for the chemical analysis of a liquid or solid sample, comprising a micropyrolyzer for heating the liquid or solid sample to produce a vapor, a chemical preconcentrator for sorption of the vapor and release of the sorbed vapor, a chemical separator for separating the chemical species of the released vapor, and a chemical detector for analysis of the chemical species in the separated vapor. Alternatively, the vapor can be injected directly into the chemical separator or the chemical detector.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 4 shows the results of pyrolysis/methylation reactions of a mixture of eight fatty acids performed with the micropyrolyzer.

FIG. 5 shows chromatograms of FAMEs produced by fatty acid pyrolysis/methylation for two different fatty acid mixtures using the micropyrolyzer.

FIG. 6 shows the results of a FAME analysis of a mixture of triglycerides using the micropyrolyzer.

FIG. 8 shows chromatograms of chemical species having specific ion fragments produced from the pyrolysis/methylation reaction of *Bacillus subtilis*.

DETAILED DESCRIPTION OF THE INVENTION

Figure 1:
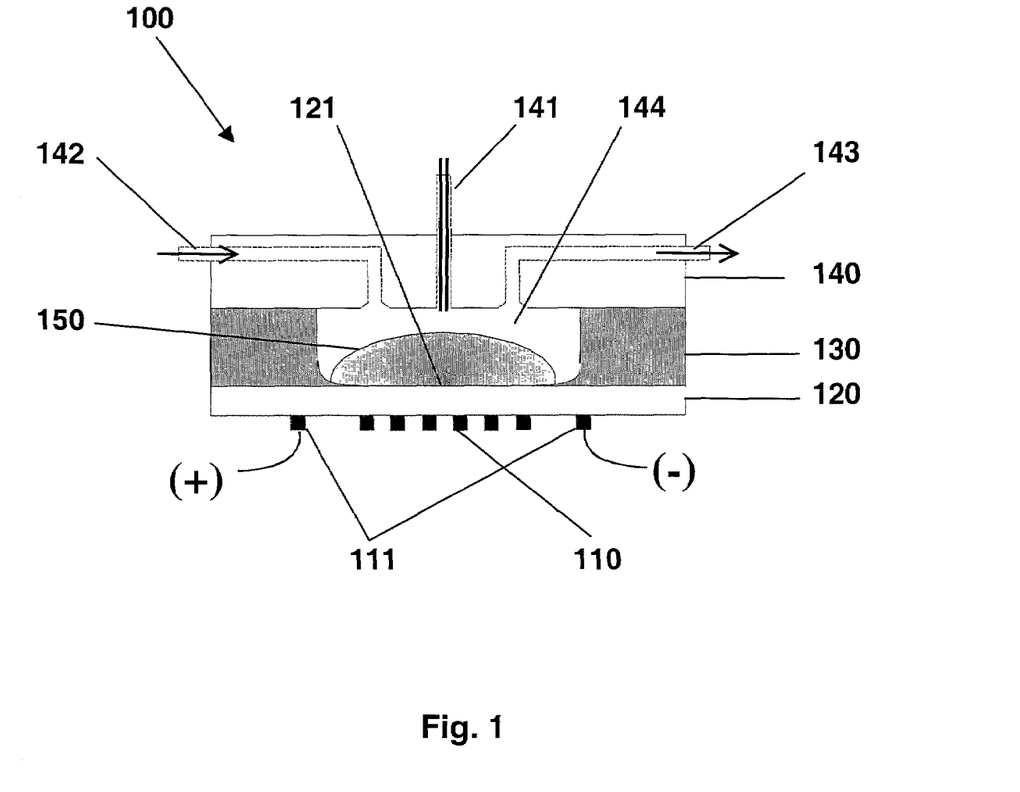
FIG. 1 shows a schematic illustration of the micropyrolyzer.

FIG. 1 shows the micropyrolyzer 100 of the present invention. The micropyrolyzer 100 comprises a resistive heating element 110 disposed on a membrane 120 suspended from a substrate 130. A gas tight lid 140 with a liquid sample inlet 141, carrier gas inlet 142, and gas outlet 143 attaches to the substrate 130. A polymeric septum (not shown) can seal the liquid sample inlet 141 to create a gas-tight seal. The liquid sample inlet 141 allows a liquid sample 150 to be deposited onto the pyrolysis stage 121. The pyrolysis stage 121 can be the upper surface of the heated membrane 120. In one embodiment of the present invention, approximately 2-3 microliters of liquid sample 150 can be accepted by the pyrolysis stage 121. Electrical contact to the resistive heating element 110 can be established with perimeter bond pads 111. The perimeter bond pads 111 and thin membrane 120 thermally and physically isolate the resistive heating element 110 and pyrolysis stage 121 from the electrical power source (not shown) and substrate 130. Alternative embodiments of the present invention can take a number of different forms, including an inlet for chemical reagents (not shown). The micropyrolyzer 100 can have an overall size of about 0.2 cm$^3$ and weight of about 1 gram, not including electronics.

The micropyrolyzer 100 can be formed by a fabrication method similar to that for the chemical preconcentrator disclosed in U.S. Pat. No. 6,171,378 to Manginell and Frye-Mason, which is incorporated herein by reference. This chemical preconcentrator comprises a sorptive material, to selectively sorb one or more chemical species from a gas or vapor over a relatively long time duration, that can be rapidly heated by a resistive heating element to release the sorbed chemical species for detection and analysis in a relatively high concentration and over a relatively short time duration. Unlike the chemical preconcentrator that is used to release a sorbed vapor, the micropyrolyzer 100 of the present invention is constructed to rapidly pyrolyze a liquid or solid sample 150 for subsequent analysis of the decomposition, dissociation, or vaporization product. Accordingly, the micropyrolyzer 100 can accommodate liquid or solid samples 150 on the pyrolysis stage 121, and there is no sorptive material disposed on the membrane 120 to concentrate chemical species from a vapor. However, with the exception of the absence of a sorptive material, the processing steps of material deposition, photolithography, masking, etching, mask stripping and cleaning required to form the micropyrolyzer 100 are similar to those disclosed by Manginell and Frye-Mason and are generally well-known in the semiconductor integrated circuit (IC) industry.

The fabrication of the micropyrolyzer 100 comprises the steps of forming a suspended membrane 120 on the substrate 130 and forming a resistive heating element 110 on the suspended membrane 120. The substrate 130 used to form the micropyrolyzer 100 generally comprises a semiconductor (e.g., silicon or gallium arsenide) or a dielectric (e.g., a glass, quartz, fused silica, a plastic, or a ceramic), with a thickness generally about 400–500 μm.

The step of forming the suspended membrane 120 comprises depositing a film on the surface of the substrate 130 and removing material from the substrate 130 underneath a portion of the deposited film. This removal can be done using either anisotropic wet etching (e.g., with potassium hydroxide) or by reactive ion etching, or by a combination of both types of etching. The suspended membrane 120 is typically formed as a rectangle or polygon with lateral dimensions from about one to a few millimeters on a side (e.g., a square of 1–3 mm on a side), or alternatively as a circle or ellipse with a size from one to a few millimeters. The suspended membrane 120 is supported at its edges by attachment to the substrate 130. The membrane 120 can be sufficiently thick (generally about 0.5–1 µm total thickness) for robustness as required for handling and to support the resistive heating element 110 and the sample 150. Additionally, the membrane 120 can be sufficiently robust to withstand any stress induced by a mismatch in thermal expansion coefficients of the membrane 120 and the supporting substrate 130 upon heating to a temperature of over several hundred ° C. Low-pressure chemically vapor deposited silicon nitride is a preferred membrane material due to its low stress, low thermal conductivity, low heat capacity, and compatibility with IC processing steps. The low thermal conductivity minimizes heat loss to the substrate 130 and the low heat capacity enables rapid heating of the pyrolysis stage 121 to elevated temperatures. Other materials such as polycrystalline silicon, silicon oxynitride, and silicon carbide can also be used to form the membrane 120.

The resistive heating element 110 generally can comprise one or more circuitous metal traces formed from one or more layers of deposited metals including platinum, molybdenum, titanium, chromium, palladium, gold, and tungsten that can be patterned on the underside of the membrane 120. Alternatively, the resistive heating element 110 can be patterned on the top side of the membrane 120 if the deposited metal is inert to or protected from the liquid or solid sample 150. To form a platinum resistive heating element 110, a 15-nm-thick layer of titanium can be deposited on the silicon nitride membrane layer 120 through a patterned photoresist mask having a circuitous opening therethrough, followed by deposition of a 100-nm-thick layer of platinum. Once the circuitous metal trace for the resistive heating element 110 has been formed, it can be annealed to relieve stress in the metal trace. If the resistive heating element 110 is patterned on the bottom side of the membrane 120, the step of forming the resistive heating element 110 is preferably performed after depositing the membrane film over the substrate 130 and before removing the substrate material to from the suspended membrane 120. This allows the resistive heating element 110 to be encapsulated in an etch-resistant material (e.g., photoresist) during the step for etching the substrate 130 and removing the substrate material from underneath the deposited membrane film. The resistive heating element 110 generally covers about 50% of the area of the suspended membrane 120 that forms the pyrolysis stage 121. An optional temperature sensor (not shown) can be located on the membrane 120 proximate to the resistive heating element 110 to aid in controlling and measuring the temperature during heating of the pyrolysis stage 121, with the temperature sensor generally comprising a circuitous metal trace (and in some instances being the resistive heating element itself) which forms a resistive temperature sensor or a thermocouple.

The resistive heating element(s) 110 can be electrically connected to a power source by a plurality of bond pads 111 for operation of the micropyrolyzer 100. The bond pads 111 can be formed, for example, of a 15-nanometer-thick layer of titanium and a 100-nanometer-thick overlayer of gold. Relatively low electrical input power is required for rapid heating of the pyrolysis stage 121, due to thermal isolation of the low-heat-capacity suspended membrane 120. Depending on the particulars of the resistive heating element 110, electrical circuitry, and the desired heating temperature profile, the typical operating voltage can be in the range of 5–20 volts. To provide a more uniform heating of the pyrolysis stage 121, an optional heat-spreading layer (e.g., comprising 0.5 µm aluminum or silicon) can be disposed over the resistive heating element 110 to improve heating uniformity and reduce thermal gradients of the pyrolysis stage 121 during heating.

The etching of the substrate 130 can provide a flow channel 144. The pyrolysis stage 121 can be fixtured with an attached glass lid 140 having a plurality of capillary tubes, including sample inlet 141 for admitting a liquid sample 150, gas inlet 142 for providing a carrier gas to the flow channel 144, and gas outlet 143 for removing the carrier gas and pyrolyzed sample vapor to a chemical analysis unit. The glass lid 140 can also have a reagent inlet (not shown) for introduction of chemical reagents to the pyrolysis stage 121.

The introduction of samples and reagents into the micropyrolyzer 100 can be accomplished in a variety of ways, including automatic deposition of liquids using microfluidic channels and pumps, front-end vapor and aerosol collection and injection, direct injection of liquid samples using a syringe or other standard inlet device, and manual placement of solid samples. Sample introduction and reagent handling functions can be either integrated into wafer-level fabrication or assembled in hybrid fashion for increased manufacturing flexibility.

For vaporization or pyrolysis applications, a rapid temperature rise of the pyrolysis stage 121 is preferred. The micropyrolyzer 100 can be repeatably temperature pulsed and has reproducible power/temperature response over time, using associated temperature control circuits. Infrared camera measurements of the temperature of an area central to the pyrolysis stage 121 of the micropyrolyzer 100 showed reproducibility of the heating temperature with heating rate. The infrared camera measurements demonstrated a temperature ramp from 85 to 290° C. in about 60 msec using 250 mW power. Temperature ramps of up to 70° C./ms have been demonstrated with the micropyrolyzer 100, with larger bias voltage resulting in faster ramps. The micropyrolyzer 100 can achieve temperatures of up to 1000° C. The micropyrolyzer 100 can withstand repeated biasing with repeatable temperature response with a 1.5 µl fatty acid sample load. In addition, a simple bias pattern can be used to combine heated chemistry followed by pyrolysis.

The method of using the micropyrolyzer 100 to vaporize or pyrolyze a liquid or solid sample 150 for analysis comprises depositing the sample 150 on the pyrolysis stage 121 of the micropyrolyzer 100, rapidly heating the sample 150 to form a vapor, and removing the vaporized product through the gas outlet 143 to a chemical analysis unit. For heated chemistry, a reagent chemical can be introduced to the sample prior to heating.

Figure 2:
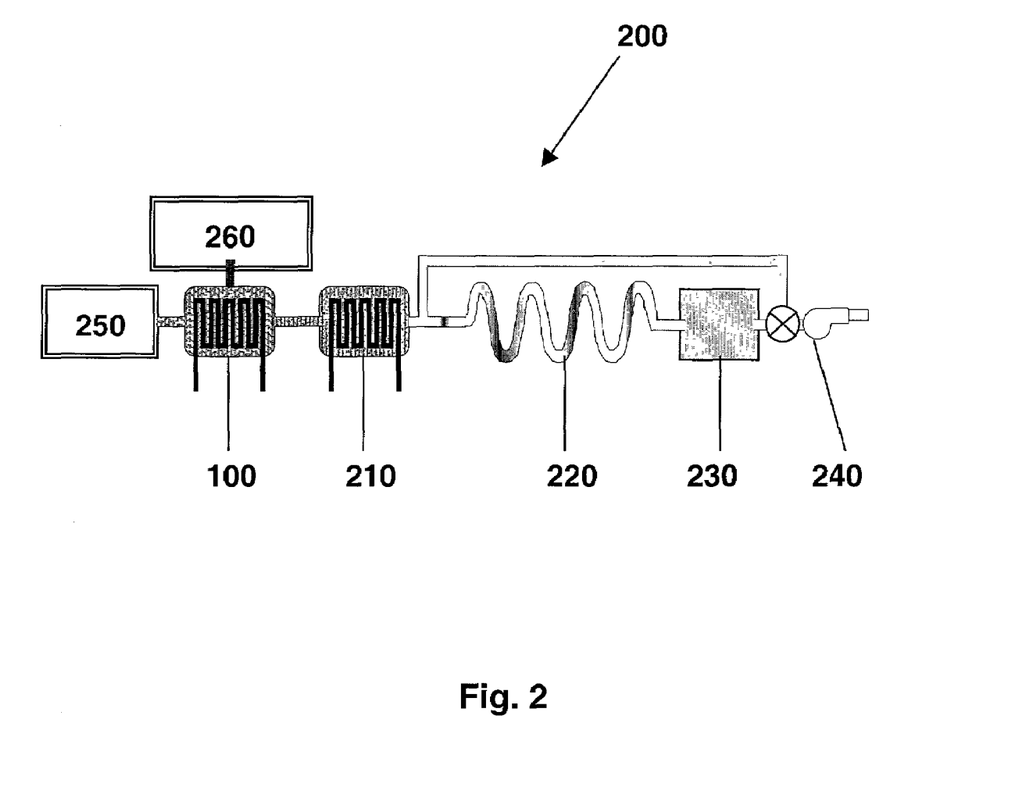
FIG. 2 shows a schematic illustration of a portable analyzer for chemical analysis of liquid or solid samples based upon the micropyrolyzer.

FIG. 2 shows a portable analyzer 200 of the present invention for chemical analysis of liquid and solid samples. The portable analyzer 200 can comprise a micropyrolyzer 100, a chemical preconcentrator 210, a chemical separator 220, and a chemical detector 230. A sample collector 250 can be attached to the micropyrolyzer 100 for introducing the liquid or solid sample 150 onto the pyrolysis stage 121. A reagent reservoir 260 can be included for introducing a derivatizing reagent. Such a portable analyzer 200 can perform a chemical analysis of a liquid or solid sample by pyrolyzing the sample with the micropyrolyzer 100 to produce a vapor, selectively sorbing the vapor on the chemical preconcentrator 210, subsequently releasing the sorbed vapor for chemical separation of the chemical species in the released vapor in the chemical separator 220, and analyzing the separated chemical species in the chemical detector 230. A vacuum pump 240 can be attached to the chemical detector 230 for removal of the analyzed species and generation of the pressure drop required to achieve sufficient flow through the analyzer 200.

Alternatively, the pyrolysis vapor from the micropyrolyzer 100 can be injected directly into the chemical separator 220 without passing through an intervening chemical preconcentrator 210. This arrangement may be desirable if, for example, the rapid vaporization of the sample 150 in the micropyrolyzer 100 alone provides adequate temporal concentration of the chemical species for effective separation in the chemical separator 220 so that additional preconcentration of the vapor in a chemical preconcentrator 210 is unnecessary. Alternatively, the vapor from the micropyrolyzer 100 or chemical preconcentrator 210 can be injected directly into the chemical detector 230 without separation of the chemical species in an intervening chemical separator 220. This arrangement may be desirable if, for example, the chemical detector 230 can selectively detect the different chemical species in the released vapor so that separation of the chemical species in a chemical separator 220 is unnecessary.

A microfabricated chemical preconcentrator 210, suitable for sorption and release of the pyrolysis vapor, has been described in the aforementioned U.S. Pat. No. 6,171,378 to Manginell and Frye-Mason. The chemical separator 220 can comprise a gas chromatograph or other vapor separation or transfer unit. A gas chromatograph relies on differential migration through a capillary column to achieve separation of the chemical species in a vapor sample. A microfabricated gas chromatograph, suitable for separation of the released vapor, has been described by Matzke et al., "Microfabricated Silicon Gas Chromatographic Micro-Channels: Fabrication and Performance" in Proceedings SPIE, Micromachining and Microfabrication Process Technology IV, 262 (1998) and U.S. Pat. No. 6,068,684 to Overton, which are incorporated herein by reference. The microfabricated gas chromatograph can comprise high-aspect-ratio microchannels etched in a silicon substrate having a stationary phase coating. The chemical detector 230 can comprise a miniature surface acoustic wave (SAW) detector, mass spectrometer, spectrophotometer, flame ionization detector, thermal conductivity detector, or other detection means. The SAW detector is a gravimetric sensor that responds to the mass of separated species accumulated in a sensing film fabricated on a semiconductor substrate. A miniature SAW detector, suitable for chemical detection of the separated species, has been described by Martin et al., "Gas Sensing with Acoustic Devices" in Proc. IEEE Ultrasonics Symposium, 423 (1996), which is incorporated herein by reference. Alternatively, the micropyrolyzer 100 can be used with a conventional, commercially available GC/MS and other chemical separators/detectors.

Experiments were performed to demonstrate the ability of the micropyrolyzer 100 to facilitate reactions of potential application in the portable analyzer 200 of the type shown in FIG. 2. Almost any type of liquid or solid sample that can form a vapor is suitable for analysis with the micropyrolyzer 100 of the present invention, comprising fatty esters, triglycerides, waxes or oils (natural/synthetic), polyunsaturated fats, fatty alcohols, phenols, dipicolinic acid, other carboxylic acid-containing molecules, alkaloidal narcotics, drugs and their metabolites, and herbicides.

An example is a set of pyrolysis/methylation reactions that are useful in the detection of bacteria using biological markers such as fatty acids. All cell membranes contain lipids that can be analyzed to create a signature to characterize biological samples and discriminate between bacteria at the class, genera, and sometimes species level. Common methods of fatty acid analysis require sample preparation that is both lengthy and labor intensive, especially for whole cell bacteria, because of their high molecular weight and low volatility. A common solution to this problem has been the use of derivatization reagents to increase the volatility of fatty acids for chemical analysis. The most widely used derivatization reaction converts the fatty acid to a more volatile fatty acid methyl ester (FAME). However, present commercial benchtop and portable analysis units still require tens of minutes for the analysis and large amounts of power for pyrolysis.

Figure 3:
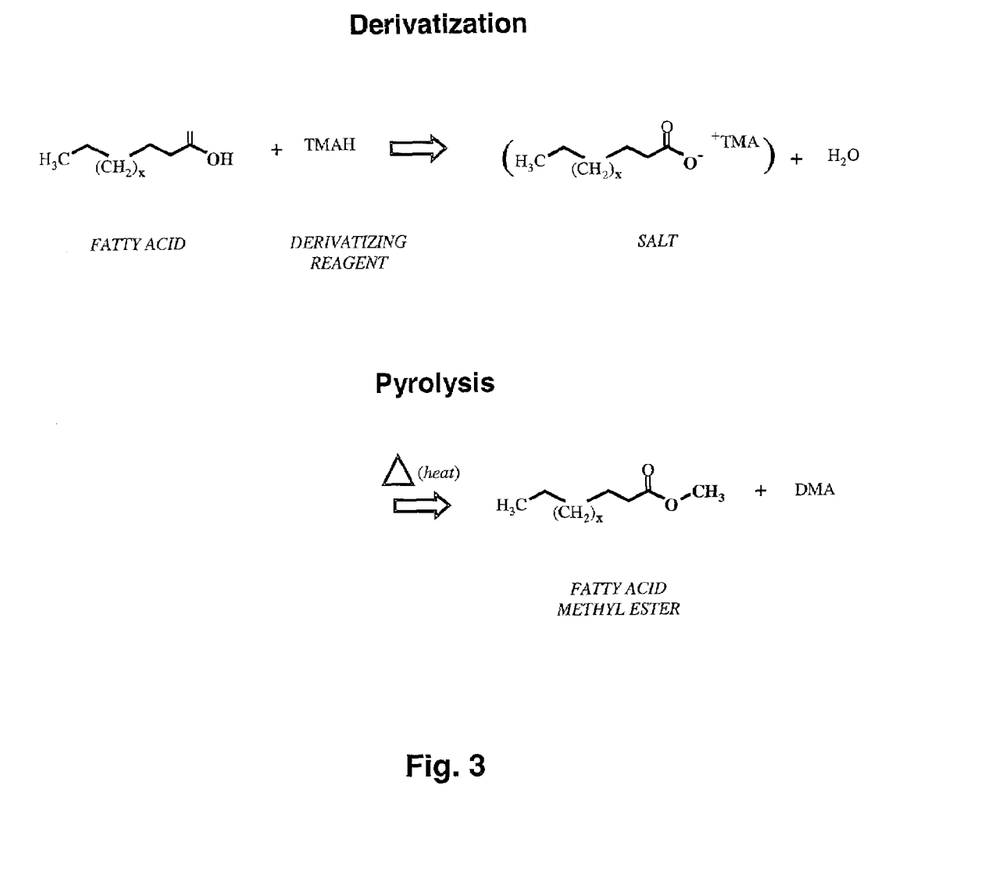
FIG. 3 shows a pyrolysis/methylation reaction of a fatty acid to its representative methyl ester.

The derivatization reaction occurs in two steps and involves both chemical reactions and pyrolysis. FIG. 3 shows one method to create FAMEs comprising mixing the derivatizing reagent tetramethylammonium hydroxide (TMAH) with the fatty acid, followed by pyrolysis of the mixture. Other common methylation reagents suitable for use with the micropyrolyzer 100 include tetramethylammonium acetate, trimethylphenylammonium hydroxide, phenyl-trimethylammonium fluoride, N,N-Dimethylformamide dimethyl acetal, and (m-trifluoro-methylphenyl) trimethylammonium hydroxide. Due to the small sample size, the pyrolysis/methylation reaction can occur much more rapidly and with lower power with the micropyrolyzer 100 of the present invention as compared to conventional pyrolyzers. In the micropyrolyzer 100, the initial chemical reaction of the fatty acid and TMAH can occur in 1–5 sec either at ambient or moderately elevated temperatures (50–100° C.) to yield a salt of the fatty acid and the derivatizing agent. Pyrolysis can then be achieved in less than 1 sec, typically at a temperature of about 370° C. or higher, completing the conversion of the fatty acid to a FAME.

Figure 4A:
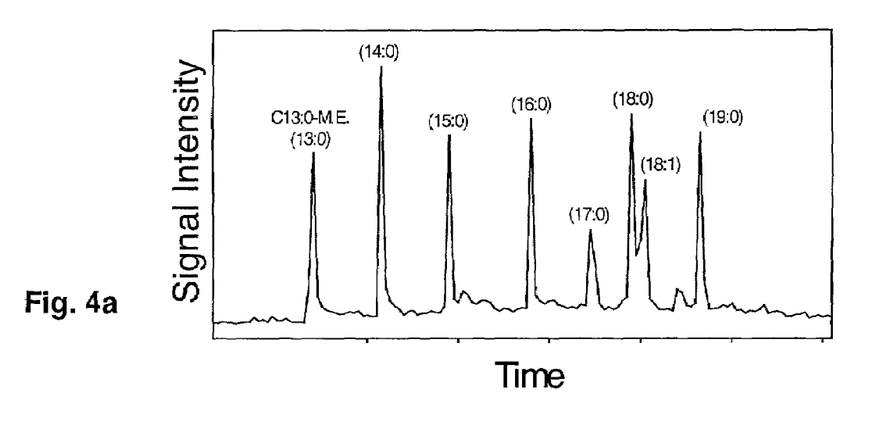
FIG. 4a shows a chromatogram of fatty acid methyl esters created by pyrolysis/methylation reaction of the mixture. Data was collected using a standard GC/MS. Fatty acid methyl ester (FAME) peaks are denoted by X:Y where X is the number of carbons and Y is the number of unsaturated bonds.

FIG. 4 shows data from a series of tests that demonstrate the ability of the micropyrolyzer 100 to facilitate the pyrolysis/methylation reaction described above. The test sample was a mixture of 8 purified fatty acids in unequal amounts solvated in methanol and chloroform. The TMAH methylating reagent was introduced onto the micropyrolyzer 100 along with the fatty acid mixture. Data was collected using a conventional GC/MS using a 15 m polar column and an electron ionization mode mass selective detector. The pyrolysis stage 121 containing the fatty acid mixture and TMAH was rapidly heated by applying a bias pulse to power the resistive heating element 110 of the micropyrolyzer 100. The transformation required less than 5 seconds for the sample preparation and reaction, after the sample was manually loaded onto the pyrolysis stage 121 and power was applied to the resistive heating element 110. The chromatogram in FIG. 4a shows elution of all expected FAME peaks from the fatty acid mixture. FAME peaks are denoted in FIG. 4a by the ratio of the number of carbons to the number of unsaturated bonds (X:Y). For example, the (C16:0) peak is a hexadecanoic acid methyl ester (or palmitic acid methyl ester) having 16 carbons and no unsaturated bonds.

Figure 4B:
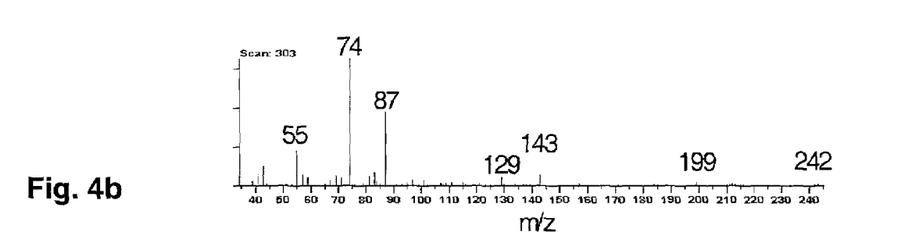
FIG. 4b shows a mass spectrum for the C14:0 methyl ester created using the micropyrolyzer.
Figure 4C:
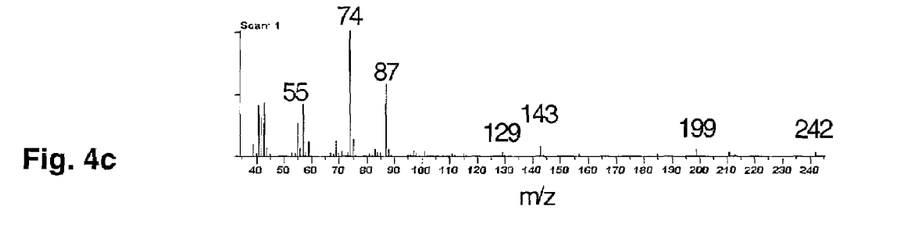
FIG. 4c shows the library mass spectrum for the C14:0 methyl ester.

A mass spectrometer can be used to identify the separated chemical species. FIGS. 4b and 4c show the mass spectra matching used to verify the presence and identification of FAME peaks in FIG. 4a. FIG. 4b shows the mass/charge spectrum of the (C14:0) peak. FIG. 4c shows the mass/charge spectrum as reported for the (C14:0) methyl ester from a mass spectra library database. All of the eluted FAME peaks had mass/charge spectra that matched the expected FAME peak from the database. No additional contamination or fatty acid peak was found. The test results in FIG. 4 demonstrate transformation and pyrolysis of the fatty acid mixture using the micropyrolyzer 100.

Figure 5A:
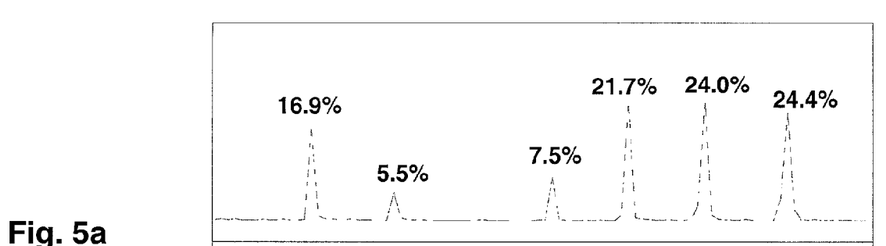
FIG. 5a shows the chromatogram of the FAMEs resulting from the derivatization reaction of a mixture containing the six fatty acids C12:C13:C15:C16:C17:C18 (all saturated) with relative concentrations of 4:1:1:4:4:4.
Figure 5B:
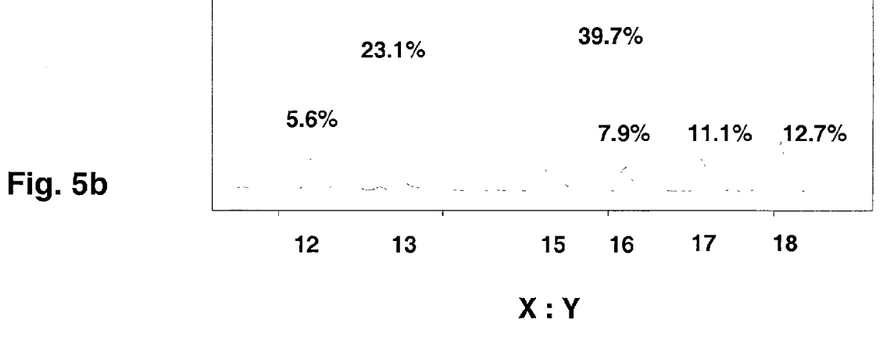
FIG. 5b shows the chromatogram of the FAMEs resulting from the derivatization reaction of a mixture containing the same six fatty acids with relative concentrations of 1:4:4:1:1:1.

FIG. 5 shows data from another test where two fatty acid mixtures were compared. FIG. 5a shows the chromatogram of the FAMEs resulting from the derivatization reaction of a mixture containing the six fatty acids C12:C13:C15:C16: C17:C18 (all saturated) with relative concentrations of 4:1: 1:4:4:4 (22.2%:5.6%:5.6%:22.2%:22.2%:22.2%), respectively. FIG. 5b shows the chromatogram of the FAMEs resulting from the derivatization reaction of a mixture containing the same six fatty acids with relative concentrations of 1:4:4:1:1:1 (8.3%:33.3%:33.3%:8.3%:8.3%:8.3%), respectively. FIGS. 5a and 5b also show the percentage peak areas calculated for each FAME peak, indicating roughly quantitative conversion of the fatty acids. These mixtures roughly simulate differences in FAME peak signatures for in situ pyrolysis/MS of two bacteria, *Pseudomonas fluorescens* and *Bacillus cereus*, respectively, seen using conventional analysis equipment.

Figure 6A:
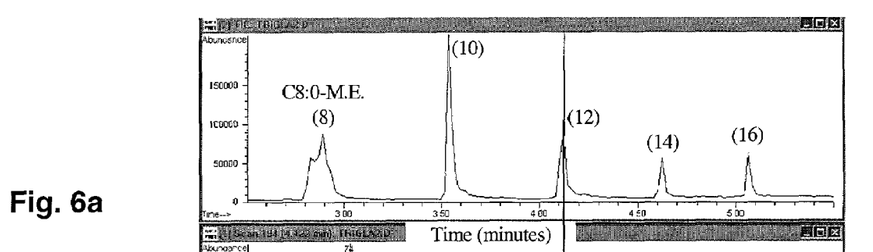
FIG. 6a shows a chromatogram from the pyrolysis/methylation of the triglyceride mixture.
Figure 6B:
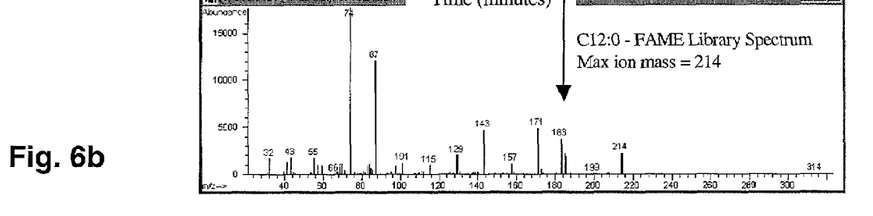
FIG. 6b shows that the mass/charge spectrum of the eluted (C12:0) FAME peak.

The FAME analysis with the micropyrolyzer 100 was also shown to work for more complex analytes containing multiple fatty acid moieties. A mixture with equal amounts of triglycerides including tricaprylin, tricaprin, trilaurin, trimyristin, and tripalmitin was pyrolyzed after treatment with TMAH in the micropyrolyzer 100. FIG. 6a shows a chromatogram from the pyrolysis/methylation of the triglyceride mixture, indicating effective transformation of the triglycerides into the five types of fatty acid moieties found in the mixture. FIG. 6b shows that the mass/charge spectrum of the eluted (C12:0) FAME peak agreed with the mass/charge spectrum as reported for the (C12:0) methyl ester from a mass spectra library database. These tests demonstrate the ability of the micropyrolyzer 100 to produce pyrolysis products that would enable the detector 230 to distinguish between bacteria at the genus level.

Figure 7:
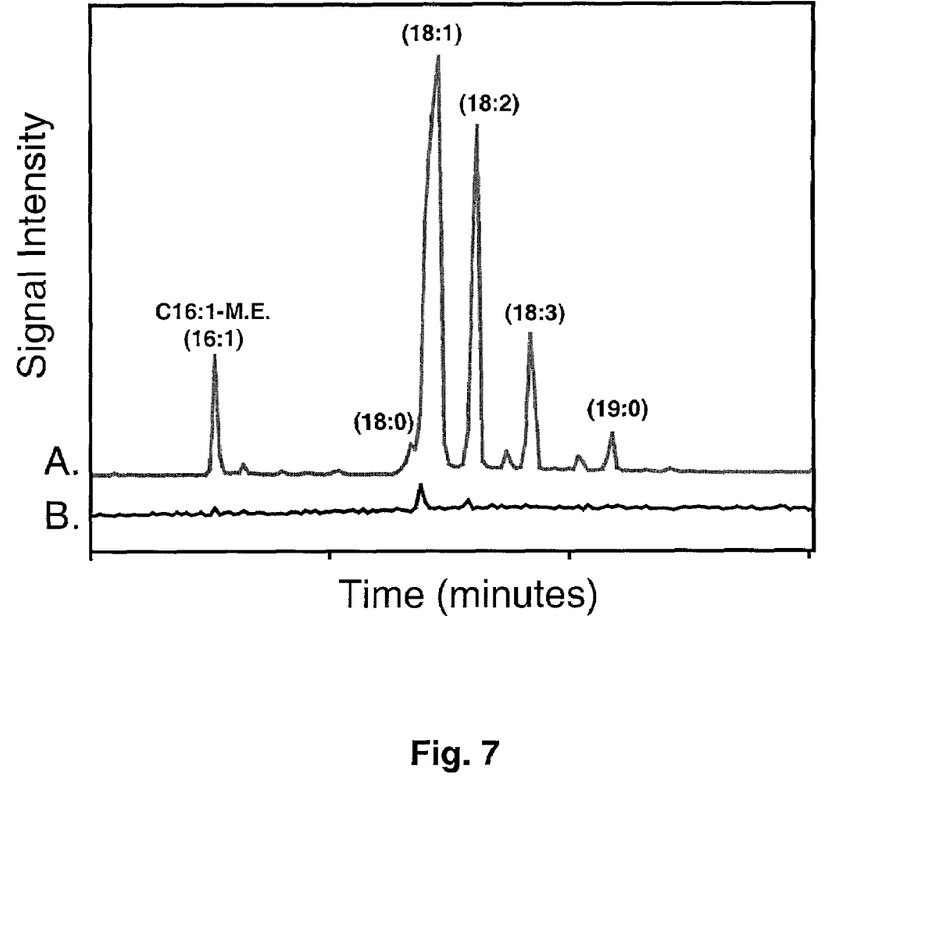
FIG. 7 shows a chromatogram of species produced by the pyrolysis/methylation reaction of Canola oil using the micropyrolyzer.

FIG. 7 shows chromatogram data, labeled "A", from the pyrolysis/methylation reaction of a 1 μl sample of Canola oil in the micropyrolyzer 100. Canola oils are one of many food types with high value fatty acid content including mainly unsaturated fats. The C18 peaks having different degrees of unsaturation are clearly separated. For comparison, a test with Canola oil and heat but no TMAH was conducted. This background scan, labeled "B", shows small residual carryover and minute FAME conversion without the use of the TMAH derivatizing reagent. This test demonstrates that the micropyrolyzer 100 can efficiently transform closely related peaks of saturated and unsaturated FAMEs.

Figure 8A:
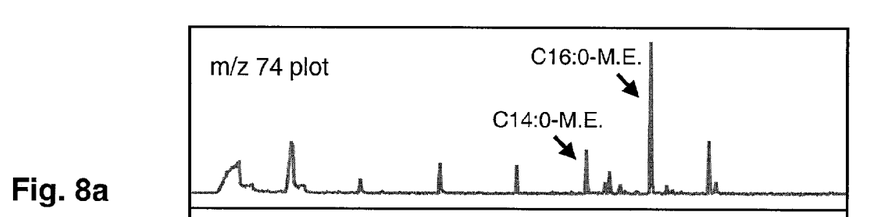
FIG. 8a shows the chromatogram for chemical species having an ion fragment with a mass-to-charge ratio of 74.
Figure 8B:
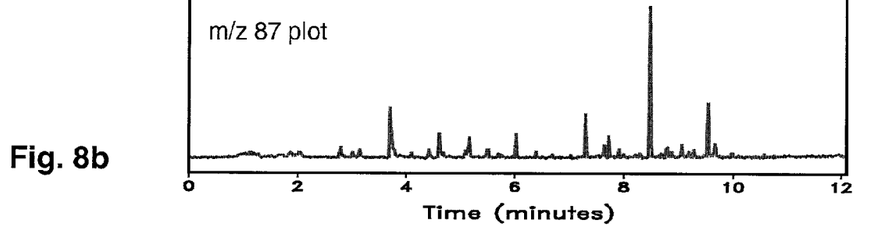
FIG. 8b shows the chromatogram for chemical species having an ion fragment with a mass-to-charge ratio of 87.

The micropyrolyzer 100 can be used to identify an unknown sample by the detection of signature chemical species in the sample. For the identification of unknown bacteria, it is useful to detect the presence of biological markers, such as fatty acids, in a bacteria-containing sample. This detection can be facilitated by observing the elution of chemical species whose mass/charge spectra have ion fragments that are characteristic of FAMEs resulting from the pyrolysis/methylation reaction of the unknown bacteria. As seen in FIGS. 4a and 4b, FAMEs produce characteristic ion fragments with mass-to-charge ratios of 74 and 87. FIG. 8a shows the elution of chemical species having ion fragments with a mass-to-charge ratio of 74, indicating the presence of FAMEs. Elution peaks for the mass 74 ion fragments of C14:0 and C16:0 methyl esters are indicated in FIG. 8a. Likewise, FIG. 8b shows the elution of chemical species having ion fragments with a mass-to-charge ratio of 87, also indicative of FAMEs. Because different bacteria have different fatty acids, the pattern of eluted FAME peaks can be used to identify the unknown bacteria in the sample. The fatty acid pattern in FIGS. 8a and 8b could be used to identify the unknown bacteria as *Bacillus subtilis*.

These pyrolysis/methylation reaction experiments demonstrate the ability of the micropyrolyzer 100 to reproduce on a microscale the types of pyrolysis that have been used with conventional pyrolyzers. However, the micropyrolyzer 100 has general applicability to the vaporization of both liquid and solid samples using various methods, including pyrolysis, heated chemistry, and thermal desorption from solids. However, unlike conventional pyrolyzers, the micropyrolyzer of the present invention can rapidly heat very small samples to high temperature and it is therefore adaptable to use in a portable analyzer.

It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for vaporizing a liquid or solid sample for analysis, comprising:
   a) providing a micropyrolyzer, comprising:
      a substrate having a suspended membrane formed thereon, the membrane having a surface for accepting the sample, wherein the substrate is selected from the group consisting of semiconductors and dielectrics; and
      a resistive heating element disposed on the membrane;
   b) depositing the sample on the sample-accepting surface of the membrane, wherein the sample comprises a fatty acid or a mixture containing fatty acids;
   c) introducing a reagent chemical to the sample, wherein the reagent chemical comprises a methylation reagent;
   d) heating the sample on the membrane with the resistive heating element to form a vapor; and
   e) removing the vapor from the micropyrolyzer for chemical analysis of the vapor.

2. The method of claim 1, wherein the sample size is less than 3 microliters.

3. The method of claim 1, wherein the sample heating rate is greater than 20° C. per millisecond.

4. The method of claim 1, wherein the sample heating rate is greater than 40° C. per millisecond.

5. The method of claim 1, wherein the sample heating rate is greater than 60° C. per millisecond.

6. The method of claim 1, wherein the sample can be heated to a temperature of up to 1000° C.

7. The method of claim 1, wherein the heating requires less than 1 Watt of power.

8. The method of claim 1, wherein the reagent chemical comprises tetramethylammonium acetate, trimethylphenylammonium hydroxide, phenyl-trimethylammonium fluoride, N,N-Dimethylformamide dimethyl acetal, or (m-trifluoro-methylphenyl) trimethylammonium hydroxide.

9. The method of claim 1, wherein the reagent chemical comprises tetramethylammonium hydroxide.

10. The method of claim 1 wherein the substrate comprises silicon.

11. The method of claim 1, wherein the membrane comprises a material selected from the group consisting of silicon nitride, polysilicon, silicon oxynitride and silicon carbide.

12. The method of claim 1, wherein the resistive heating element comprises a circuitous metal trace.

13. The method of claim 12, wherein the metal comprises a metal selected from the group consisting of platinum, molybdenum, titanium, chromium, palladium, gold, tungsten, and combinations thereof.

* * * * *